United States Patent
Rogers

(10) Patent No.: US 9,976,925 B2
(45) Date of Patent: May 22, 2018

(54) APPARATUS AND METHOD FOR TESTING LINEAR THERMAL SENSORS

(71) Applicant: Kidde Technologies Inc., Wilson, NC (US)

(72) Inventor: Aaron Stanley Rogers, Surf City, NC (US)

(73) Assignee: Kidde Technologies, Inc., Wilson, NC (US)

( * ) Notice: Subject to any disclaimer, the term of this patent is extended or adjusted under 35 U.S.C. 154(b) by 406 days.

(21) Appl. No.: 14/885,436

(22) Filed: Oct. 16, 2015

(65) Prior Publication Data

US 2017/0108395 A1 Apr. 20, 2017

(51) Int. Cl.
*G01N 29/07* (2006.01)
*G01M 3/00* (2006.01)

(52) U.S. Cl.
CPC .................. *G01M 3/002* (2013.01)

(58) Field of Classification Search
CPC .... G10K 11/341; G01K 15/007; G01N 29/07; G01N 29/075; G01N 29/11; G01N 29/346; G01N 29/341; G01N 29/345; G01R 31/11
USPC ............................ 374/1, 4, 120, 117; 702/39
See application file for complete search history.

(56) References Cited

U.S. PATENT DOCUMENTS

| | | | | |
|---|---|---|---|---|
| 3,715,710 A | * | 2/1973 | Bernstein | B06B 1/0215 367/137 |
| 4,160,228 A | * | 7/1979 | Hix | G01V 13/00 181/110 |
| 4,372,693 A | | 2/1983 | Lutz | |
| 4,483,630 A | * | 11/1984 | Varela | G01K 11/22 374/117 |
| 4,772,131 A | * | 9/1988 | Varela | G01K 11/24 374/119 |
| 4,857,928 A | * | 8/1989 | Gailus | H04B 14/062 341/143 |
| 5,294,909 A | | 3/1994 | Frazier | |
| 5,410,208 A | * | 4/1995 | Walters | B06B 1/0622 310/334 |

(Continued)

FOREIGN PATENT DOCUMENTS

WO 2009046751 A1 4/2009

OTHER PUBLICATIONS

Extended European Search Report, for European Patent Application No. 16194010.1, dated Feb. 15, 2017, 5 pages.

*Primary Examiner* — Gail Kaplan Verbitsky
(74) *Attorney, Agent, or Firm* — Kinney & Lange, P.A.

(57) ABSTRACT

A linear-thermal-sensor testing system has a signal generator and a reflection analyzer. The signal generator generates a series of damped sinusoidal impulse signals each of a different frequency, and transmits the damped sinusoidal impulse signals to a first end of the linear thermal sensor. The linear thermal sensor generates a reflection signal corresponding to each of series the damped sinusoidal impulse signals at a plurality of electrical discontinuities in the linear thermal sensing array. The reflection analyzer receives a reflection signal from the first end of the linear thermal sensor. The reflection signal has indicia of electrical properties and locations within the linear thermal sensor for each of the plurality of electrical discontinuities. The reflection analyzer calculates the electrical properties and the locations within the linear thermal sensor based on the indicia of the received reflection signal.

22 Claims, 13 Drawing Sheets

(56) References Cited

U.S. PATENT DOCUMENTS

| | | | |
|---|---|---|---|
| 5,793,293 A | 8/1998 | Melamud et al. | |
| 6,326,598 B1 | 12/2001 | Carvalho et al. | |
| 7,356,438 B2 | 4/2008 | Schaumann et al. | |
| 8,109,298 B2 | 2/2012 | Rostek et al. | |
| 8,708,554 B2 | 4/2014 | Thompson et al. | |
| 2003/0009300 A1 | 1/2003 | Giurgiutiu | |
| 2007/0123776 A1* | 5/2007 | Aharoni | A61B 5/02007 600/437 |
| 2013/0023767 A1* | 1/2013 | Mammone | A61B 8/0825 600/440 |
| 2013/0139598 A1 | 6/2013 | Sohn et al. | |
| 2015/0122029 A1* | 5/2015 | Suzuki | G01N 29/043 73/620 |
| 2016/0220230 A1* | 8/2016 | Rice | B06B 1/0662 |

* cited by examiner

APPARATUS AND METHOD FOR TESTING LINEAR THERMAL SENSORS

BACKGROUND

Exhaust gases and/or compressed air from aircraft engines can be used for many purposes. Exhaust gases can be ported to drive impellers of pneumatic motors to provide energy. These impeller driven motors may perform various mechanical functions, such as generate electricity, pump gases, rotate shafts, etc. Exhaust gases can be ported to provide heat in locations remote from the aircraft's engines. Exhaust gases can be used as part of a temperature regulation system to maintain an atmospheric environment in temperature sensitive locations of an aircraft. Compressed air can be used for cabin pressurization or as a source for pneumatic control systems.

Both the exhaust gases and the compressed air can be very hot, as exhaust gases are the product of an exothermic chemical reaction, and pressurization raises the temperature of the air being compressed. Various plenums, manifolds, and ductworks can be used to route these exhaust gases from the engines to the various locations of the aircraft that require their use. It may be desirable, to localize the high temperature of the gases to locations immediately surrounding these plenums, manifolds and ductworks. Should these plenums, manifolds, and ductworks fail so as to permit the exhaust gases and/or compressed air to leak, deleterious effects may arise.

Linear thermal sensors can be located adjacent to and along these plenums, manifolds, and ductworks that carry hot exhaust gases and/or compressed air. Such linear thermal sensors can provide a monitoring function of the temperature immediately adjacent to the plenums, manifolds, and ductworks at locations traversed by the linear thermal sensors. Should these linear thermal sensors indicate a temperature at a specific location that is greater than a predetermined threshold, pilots of the aircraft can be notified as to the sensed over-temperature condition.

Linear thermal sensors can be used in various locations besides aircraft. For example, linear thermal sensors can be used in ground-based, marine, and/or aerospace applications. These sensors are particularly useful if detection of overheat events is required along a linear path. Known methods for testing linear thermal sensors yield less than optimal results. And known systems that interface with linear thermal sensors and sensor arrays have encountered difficulties in detecting thermal events beyond a first electrical discontinuity.

SUMMARY

Apparatus and associated methods relate to a linear-thermal-sensor testing system that includes a signal generator that is configured to generate a series of damped sinusoidal impulse signals each of a different frequency, and transmit the damped sinusoidal impulse signals to a first end of a linear thermal sensor. The linear thermal sensor is configured to generate a reflection signal corresponding to each of the series of damped sinusoidal impulse signals at one or more electrical discontinuities in the linear thermal sensor. The linear-thermal-sensor testing system includes a reflection analyzer that is configured to receive a reflection signal from the first end of the linear thermal sensor. The reflection signal has indicia of electrical properties and locations within the linear thermal sensor for each of the one or more electrical discontinuities. The reflection analyzer is further configured to calculate the electrical properties and the locations within the linear thermal sensor based on the indicia of the received reflection signal.

In some embodiments, a method of testing a linear thermal sensor includes the step of generating a series of damped sinusoidal impulse signals each of a different frequency. The method includes the step of transmitting the generated series of damped sinusoidal impulse signals to a first end of the linear thermal sensor. The method includes the step of receiving, at the first end of the linear thermal sensor, a series of reflection signals each corresponding to a one of the series of damped sinusoidal impulse signals. Each of the reflection signals is reflected by one or more electrical discontinuities in the linear thermal sensor. The method includes the step of determining an amplitude of the received reflected signal. The method includes the step of determining a time-delay of the received reflected signal. The method includes the step of calculating an electrical property of an electrical discontinuity in the linear thermal sensor based on the determined amplitude and phase shift of the received reflected signal.

DETAILED DESCRIPTION

Figure 1:
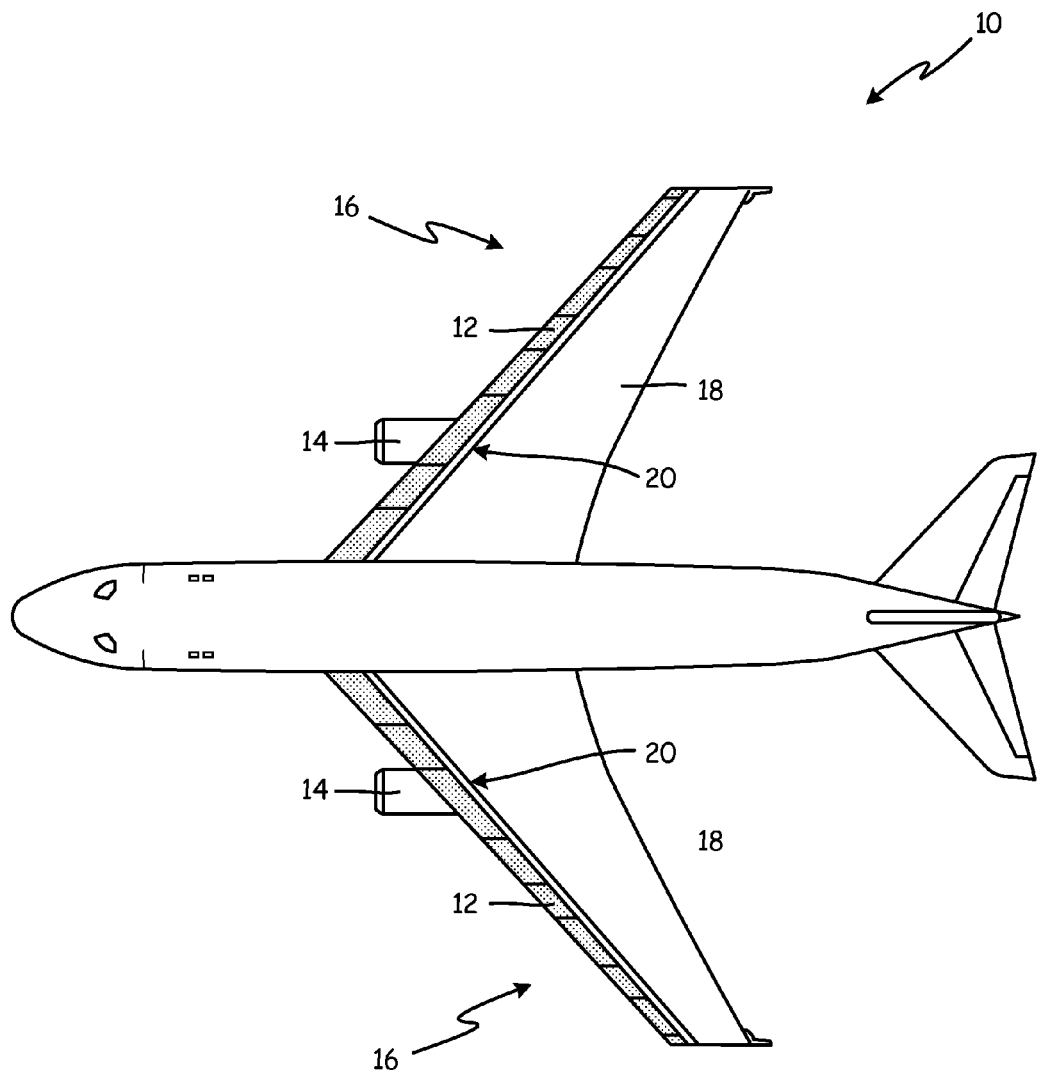
FIG. 1 is a plan view of an exemplary aircraft that has a hot air duct and a linear thermal sensor monitoring the hot air duct for leaks.

FIG. 1 is a plan view of an exemplary aircraft that has a hot air duct and a linear thermal sensor monitoring the hot air duct for leaks. In the FIG. 1 depiction, aircraft 10 includes hot air ducts 12 that provide a fluid path for exhaust gases generated in engines 14 along leading edges 16 of wings 18. Proximate each of hot air ducts 12 is linear thermal sensor 20. Hot air ducts 12 can provide a fluid path for exhaust gases along leading edges 16 to provide de-icing capability, for example. Linear thermal sensors 20 run adjacent to and along hot air ducts 12 so as to monitor temperature adjacent to and along hot air ducts 12. Linear thermal sensors 20 can be used for detecting leaks in hot air ducts 12. Signals transmitted in linear thermal sensors 20 can contain indicia which can be used to provide a precise location where linear thermal sensors 20 experience an over-temperature condition—a temperature that exceeds a predetermined threshold.

Figure 2:
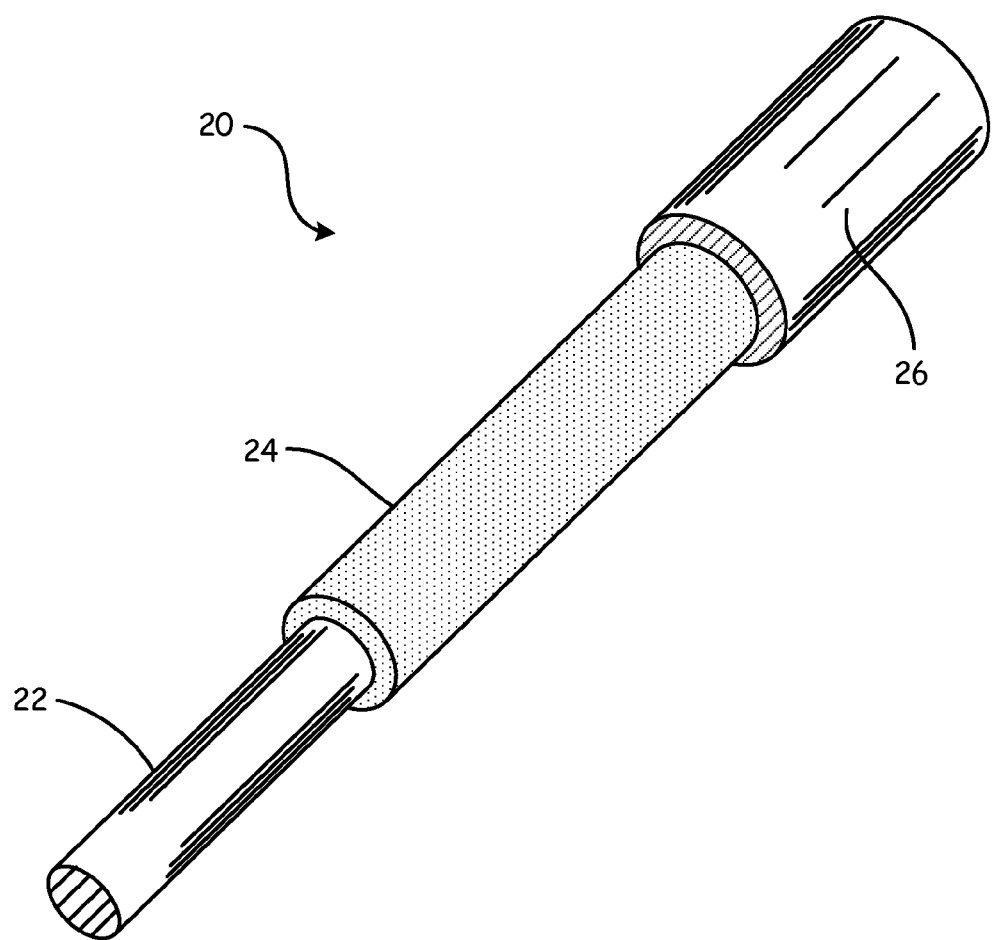
FIG. 2 is a perspective view of an exemplary coaxial eutectic-salt type of linear thermal detector.

FIG. 2 is a perspective view of an exemplary coaxial eutectic-salt type of linear thermal detector. In FIG. 2, exemplary linear thermal detector 20 includes inner conductor 22, porous insulator 24 and outer conductive tubing 26 arranged in coaxial fashion. Porous insulator 24 can be saturated with a eutectic salt or dielectric semiconductor media. Various chemistries of eutectic salts can be used. The eutectic salt can have a high resistance when in a solid phase and a low resistance when in a liquid phase, for example. Thus, if everywhere along a length of linear thermal detector 20 is at a temperature that is less than a melting temperature of the eutectic salt that saturates porous insulator 24, then inner conductor 22 and outer conductive tubing 26 will be substantially electrically isolated from one another. If, however, a location along a length of liner thermal sensor 20 is subjected to a temperature greater than the melting temperature of the eutectic salt that saturates porous insulator 24, then electrical conduction will be facilitated between inner conductor 22 and outer conducive tube 26 via conduction through the melted eutectic salt.

Various compositions of eutectic salts or dielectric semiconductor media can be used, each with a particular melting temperature specific to the composition of the eutectic salt. Various methods of filling or saturating porous insulator 24 can be performed. For example, aerosol spray coating over the porous insulator 24 can be performed before cladding porous insulator 24 with outer conductive tubing 26. Porous insulator 24 can be dip coated before cladding porous insulator 24 with outer conductive tubing 26. And after cladding porous insulator 24 with outer conductive tubing 26, porous insulator 24 can be saturated with the eutectic salt using vacuum fill draw methods.

Each manufacturing method and each material configuration can present its own challenge. Porous insulator 24 can be made of a ceramic material, for example. Various ceramic materials can be used, some of which being brittle. Should porous insulator 24 be broken, electrical parameters of linear thermal sensor may differ at a location of such a break from those where porous insulator 24 is unbroken. Any of the eutectic salt coating methods may inadvertently result in discontinuities of saturation and/or voids in the semiconducting media or in the eutectic salt. Voids and/or discontinuities can be problematic for one or more reasons. For example, wherever a void exists, linear thermal sensor 20 can be insensitive to detecting an overheat event, because a state-change of eutectic salt cannot occur where no eutectic salt exists. Each electrical discontinuity will reflect an incident impulse signal used in traditional Time Domain Reflectometry (TDR) methods. When traditional TDR is used to provide a location of an overheat event, such reflections can result in false alarms, for example.

Because of these and other problems, linear thermal sensors 20 can be tested to determine if any voids and/or discontinuities are present. Linear thermal sensors 20 can be thermally mapped, for example. Thermal mapping can involve heating a location at a first end of linear thermal sensor 20 until the eutectic salt melts. Then an adjacent location is heated until the eutectic salt melts. Each location between the first end and a second end of linear thermal sensor 20 is heated to a temperature above the melting point of the eutectic salt to ensure that there are no voids in the saturation of porous insulator 24. Such a thermal mapping process can be time consuming and/or expensive.

Figure 3:
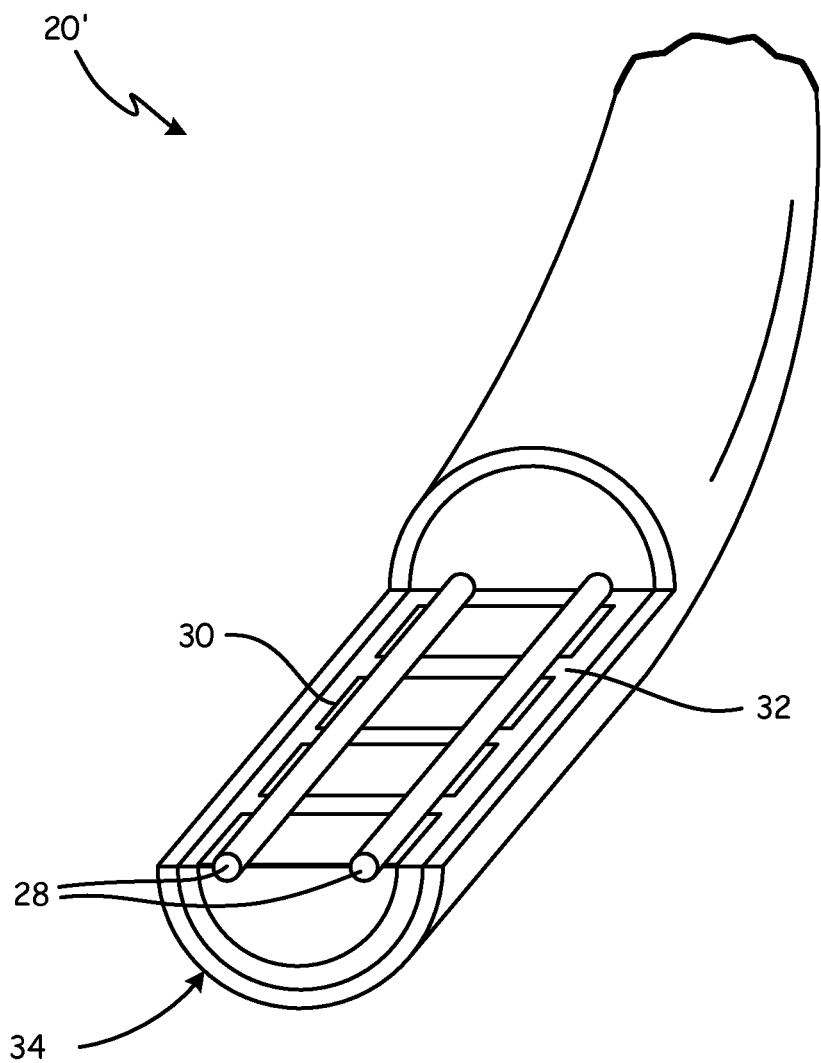
FIG. 3 is a perspective view of an exemplary thermistor type of linear thermal detector.

FIG. 3 is a perspective view of an exemplary thermistor type of linear thermal detector. In FIG. 3, exemplary linear thermal detector 20' includes wires 28 each contacting an opposite end of thermistor beads 30. Separating adjacent thermistor beads 30 is silicate filler 32. Sheath 34 surrounds silicate filler 32, thermistor beads 30, and wires 28. Thermistor beads 30 have electrical resistances that change as a function of temperature. The resistance between conductors 28 is thus indicative of the temperature of thermistor beads 30.

Figure 4A:
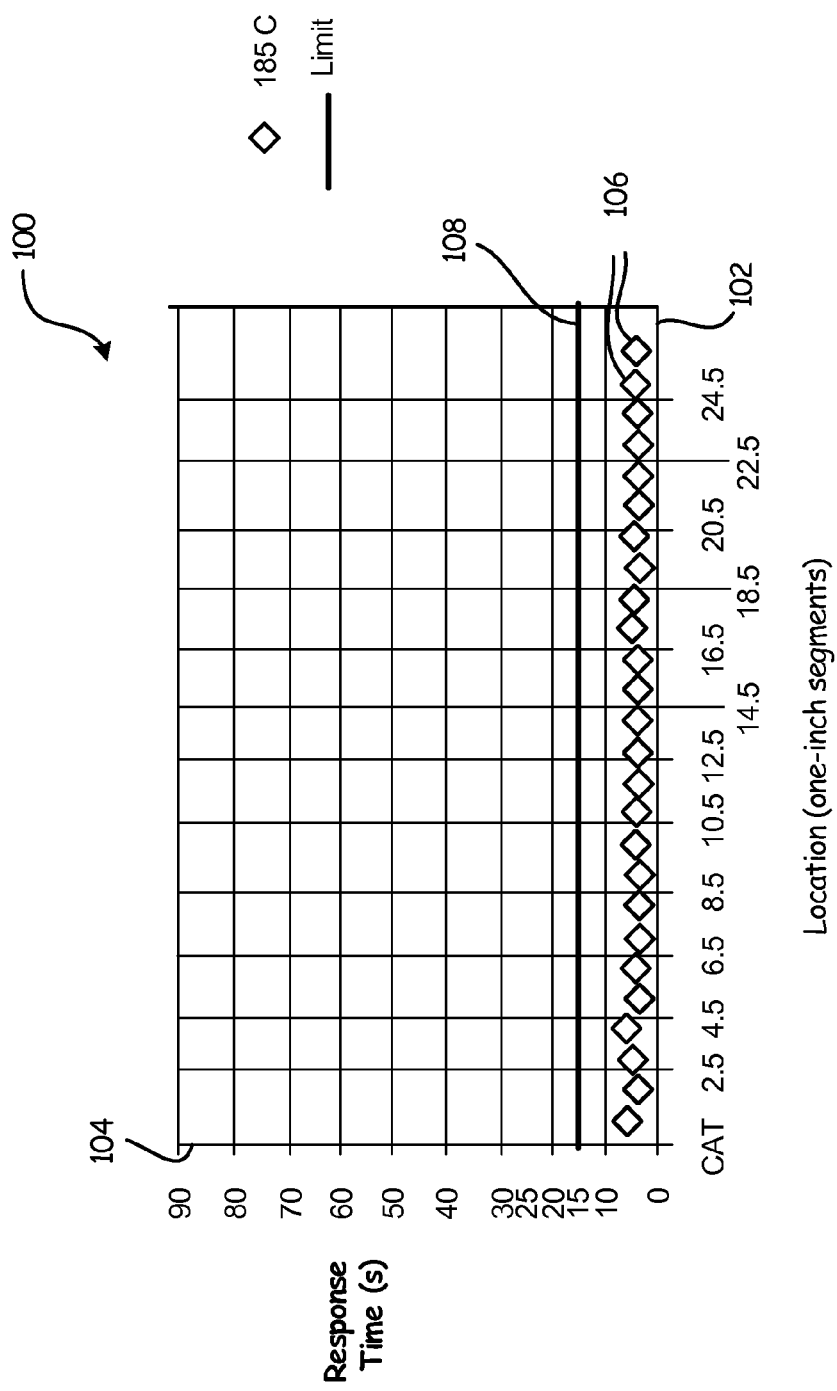
FIGS. 4A-4B are graphs of thermal mapping and traditional Time Domain Reflectometry (TDR) of an exemplary linear thermal sensor that is substantially uniform throughout, respectively.
Figure 4B:
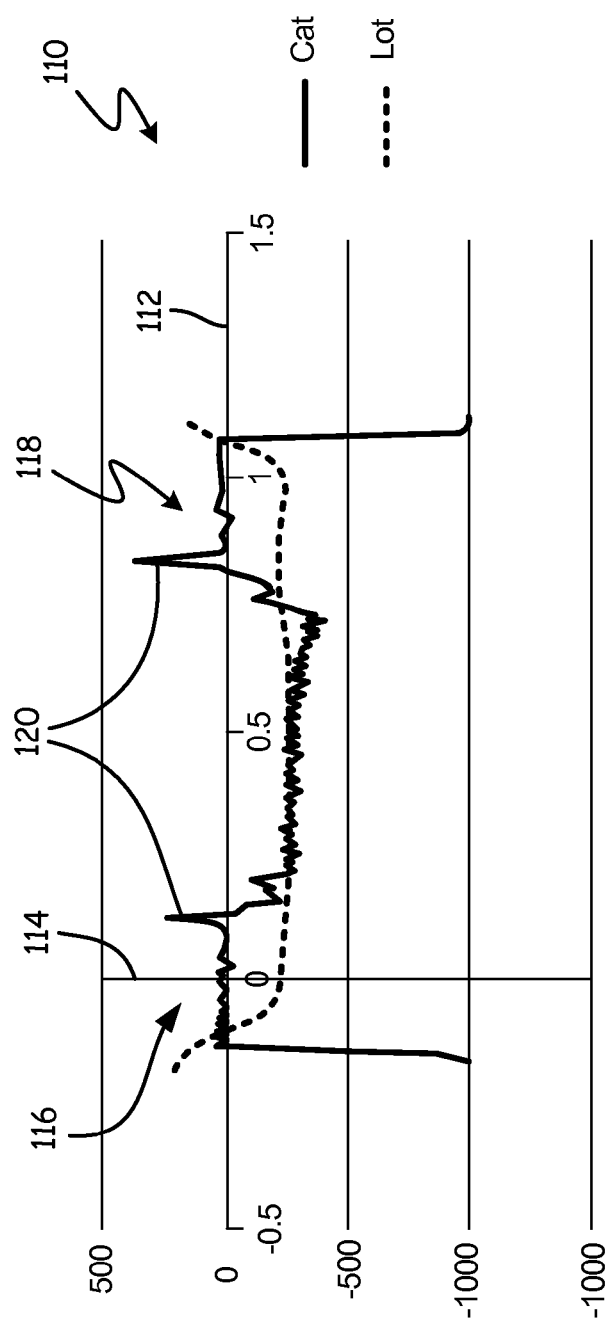

FIGS. 4A-4B are graphs of thermal mapping and traditional Time Domain Reflectometry (TDR), respectively, of an exemplary linear thermal sensor that is substantially uniform throughout. In FIG. 4A, graph 100 has horizontal axis 102, which represents locations (in units of length) along a length of linear thermal sensor 20. Graph 100 has vertical axis 104, which represents response times (in units of seconds) for melting of the eutectic salt to occur using a heating source. Graph 100 has a series of experimental data 106 plotted thereon. Each datum 106 indicates the heating time required at a particular location along a length of linear thermal sensor 20 until melting is detected via electrical conductivity between inner conductor 22 and outer conductive tube 26 rises above a threshold level. This figure indicates melting of the eutectic salt at about five seconds of heating for every tested location along the length of linear thermal sensor 20.

In FIG. 4B, graph 110 shows traditional TDR response curves 116, 118 using the same linear thermal sensor 20 that was thermally mapped in FIG. 4A. Graph 110 has horizontal axis 112, which represents time. Graph 110 has vertical axis 114 which represents magnitudes of reflection signals. Graph 110 has experimental data 116, 118 plotted thereon. Experimental data 116 represents a magnitude of a reflection signal measured from a first end of linear thermal sensor 20. At a time of about 0.15 seconds, peak 120 in reflection signal data 116 is measured. Peak 120 corresponds to an electrical discontinuity associated with signal insertion into a first end of linear thermal sensor 20. Then at times after peak 120 occurs, reflection signal 116 is substantially constant until peak 122 is measured. Peaks 122 of reflection signal data 116, 118, respectively, indicate a reflection from an open terminal end of linear thermal sensor 20. Reflections signal data 118 is aligned with and graphed in reverse to reflection signal data 116, each data set 116, 118 indicating the same information but measured from an opposite end of linear thermal sensor 20. Note that other than peaks 120, 122 no other significant peaks are exhibited, indicating that no significant electrical discontinuities other than an insertion discontinuity and a terminal discontinuity on two opposing ends of linear thermal sensor 20 are detected.

Figure 5A:
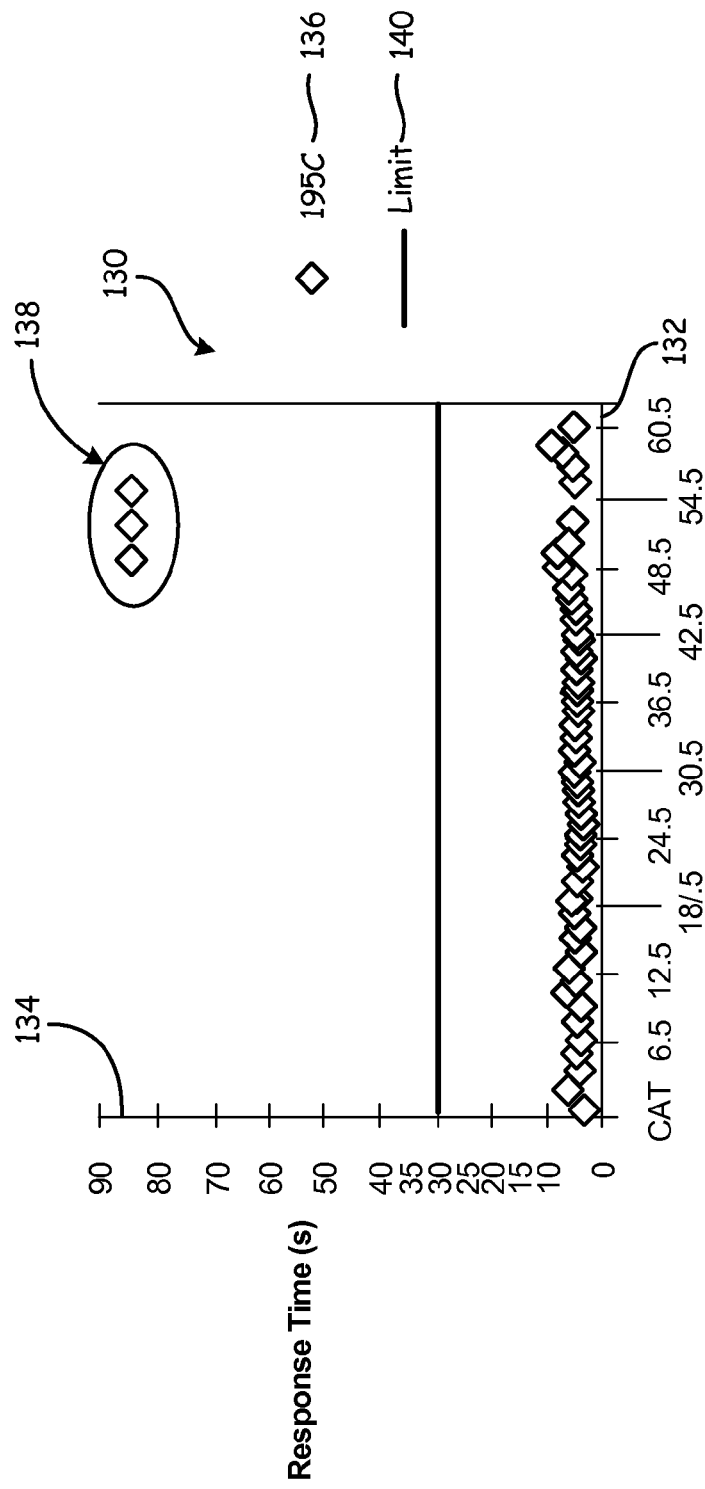
FIGS. 5A-5B are graphs of thermal mapping and traditional Time Domain Reflectometry (TDR) of an exemplary linear thermal sensor that has an electrical discontinuity, respectively.
Figure 5B:
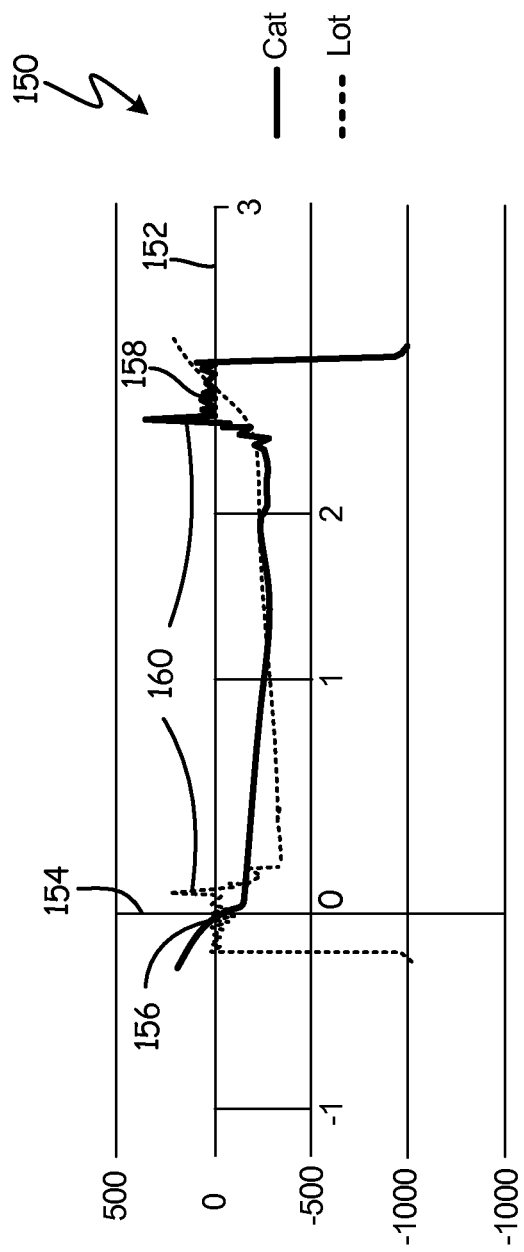

FIGS. 5A-5B are graphs of thermal mapping and traditional Time Domain Reflectometry (TDR), respectively, of an exemplary linear thermal sensor that has an electrical discontinuity. In FIG. 5A, graph 130 has horizontal axis 132, which represents locations (in units of length) along a length of linear thermal sensor 20. Graph 130 has vertical axis 134, which represents response times (in units of seconds) for melting of the eutectic salt to occur using a heating source. Graph 130 has a series of experimental data 136 plotted thereon. Each datum 136 indicates the heating time required at a particular location along a length of linear thermal sensor 20 until melting is detected via electrical conductivity between inner conductor 22 and outer conductive tube 26 rises above a threshold level. Note that in region 138 of graph 130, data 136 indicates that a long heating time is required before melting of the eutectic salt is detected. Data 136 in region 138 may simply indicate the time-out condition when the test ends, and perhaps the conductivity condition for melting has not been met before the time-out condition. Such a long heating time can be indicative of a void of eutectic salt in a region of linear thermal sensor 20 corresponding to the x-coordinates (i.e., location coordinates) of region 138. This figure indicates melting of the eutectic salt at about five seconds of heating for all tested locations outside of region 138. Outside of region 138 the eutectic salt seems present as indicated by the normal testing times.

In FIG. 5B, graph 150 shows traditional TDR response curves 156, 158 using the same linear thermal sensor 20 that was thermally mapped in FIG. 5A. Graph 150 has horizontal axis 152, which represents time. Graph 110 has vertical axis 154 which represents magnitudes of reflection signals. Graph 150 has experimental data 156, 158 plotted thereon. Experimental data 156 represents a magnitude of a reflection signal measured from a first end of linear thermal sensor 20. At a time of about 0.15 seconds, peak 160 in reflection signal data 156 is measured. Peak 160 corresponds to an electrical discontinuity associated with signal insertion into a first end of linear thermal sensor 20. Then at times after peak 160 occurs, reflection signal 156 is substantially constant until peak 162 is measured. Peak 162 of reflection signal data 156 indicates a reflection from an open terminal end of linear thermal sensor 20. Reflections signal data 158 is aligned with and graphed in reverse to reflection signal data 156, each data set 156, 158 indicating the same information but measured from an opposite end of linear thermal sensor 20. Note that other than peaks 160, 162 no other significant peaks are exhibited, indicating that no significant electrical discontinuities other than an insertion discontinuity and a terminal discontinuity on two opposing ends of linear thermal sensor 20 are detected. But in this example, a known electrical discontinuity exists at locations corresponding to x-coordinates of region 138 in FIG. 5A. Thus, traditional TDR measurements fail to detect such electrical discontinuities.

Not only do traditional TDR measurement techniques fail to detect electrical discontinuities corresponding to eutectic salt voids in linear thermal sensors, but traditional TDR measurement techniques can be unsatisfactory for other reasons. For example, traditional TDR measurement techniques can use impulse signals that do not traverse a first electrical discontinuity with sufficient energy to reliably detect subsequent electrical discontinuities. Sinusoidal impulse signals, however, of frequencies tuned to traverse a specific electrical discontinuity can "look beyond" a first electrical discontinuity. Traditional TDR measurement techniques use impulse signals that have fast edges and/or DC content. Fast edges and/or DC content can damage the molecular structure of eutectic salts and/or dielectric semiconductor media. Damped sinusoidal impulse signals, however, with edges that have maximum slopes of a magnitude less than a predetermined threshold will not damage the media of linear thermal sensors. Damped sinusoidal impulse signals that have substantially no DC content will provide signal stimuli without damaging the media of linear thermal sensors.

Figure 6:
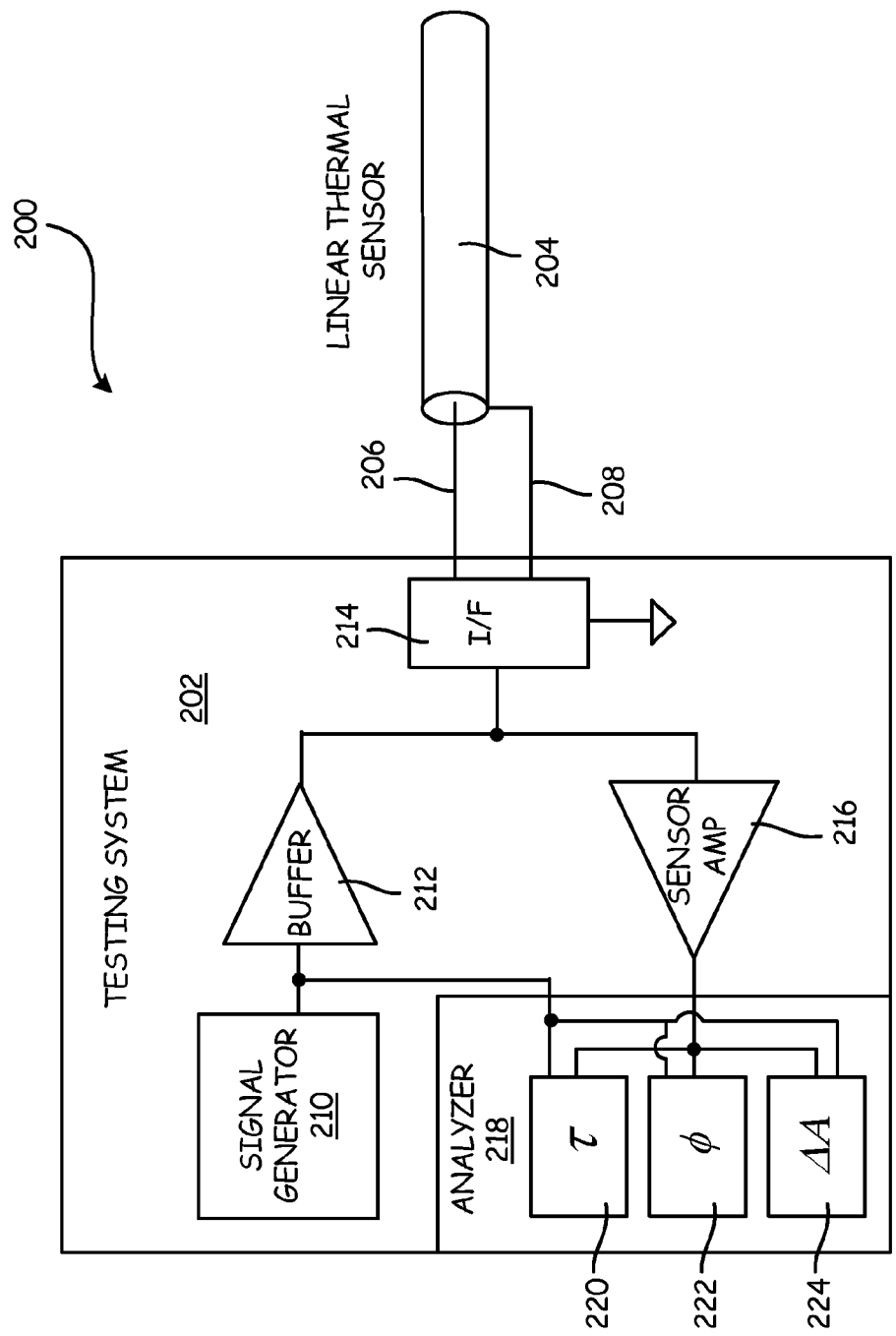
FIG. 6 is a block diagram of an exemplary testing system for linear thermal sensors.

FIG. 6 is a block diagram of an exemplary testing system for linear thermal sensors. In FIG. 6, block diagram 200 includes testing system 202 and linear thermal sensor 204 electrically connected to one another via connection lines 206, 208. Testing system 202 includes signal generator 210, buffer/amplifier 212, input/output interface 214, sense amplifier 216, and signal analyzer 218. Exemplary signal analyzer 218 includes reflection time delay detector 220, reflection phase detector 222, and reflection amplitude detector 224.

In the depicted embodiment, signal generator 210 generates a damped sinusoidal impulse signal. The damped sinusoidal impulse signal can have between 2 and 10 periods of a sinusoid. In some embodiments, the damped sinusoidal impulse signal can have between 3 and 5 periods. The damped sinusoidal impulse signal can be amplitude modulated by an amplitude envelope. The amplitude envelope can be a damped amplitude envelope that results in a first cycle having an amplitude that is larger than an amplitude of subsequent cycles, for example. In some embodiments, each of subsequent cycles after the first cycle can have an amplitude that is less than or equal to the amplitude of all cycles preceding it.

The generated signal is then amplified and/or buffered by buffer/amplifier 212. The buffered/amplified signal is then delivered to the linear thermal sensor via input/output interface 214. The signal then travels along a length 226 of linear thermal sensor 204. The signal will be reflected at locations that mark electrical discontinuities. The reflected signal will then be communicated to sense amplifier 216 via input/output interface 214. Signal analyzer 218 will then compare the reflected signal with the generated signal. Differences between the reflected signal and the generated signal may include a time delay, a phase difference, and/or an amplitude difference. Each of these differences can be measured in the depicted embodiment. The signal delivered to signal analyzer 218 via sense amplifier 216 may include portions of the generated signal and portions of the reflected signal. Signal analyzer 218 can distinguish these portions by comparing the signal delivered by sense amplifier 216 to the generated signal provided by signal generator 210.

Figure 7:
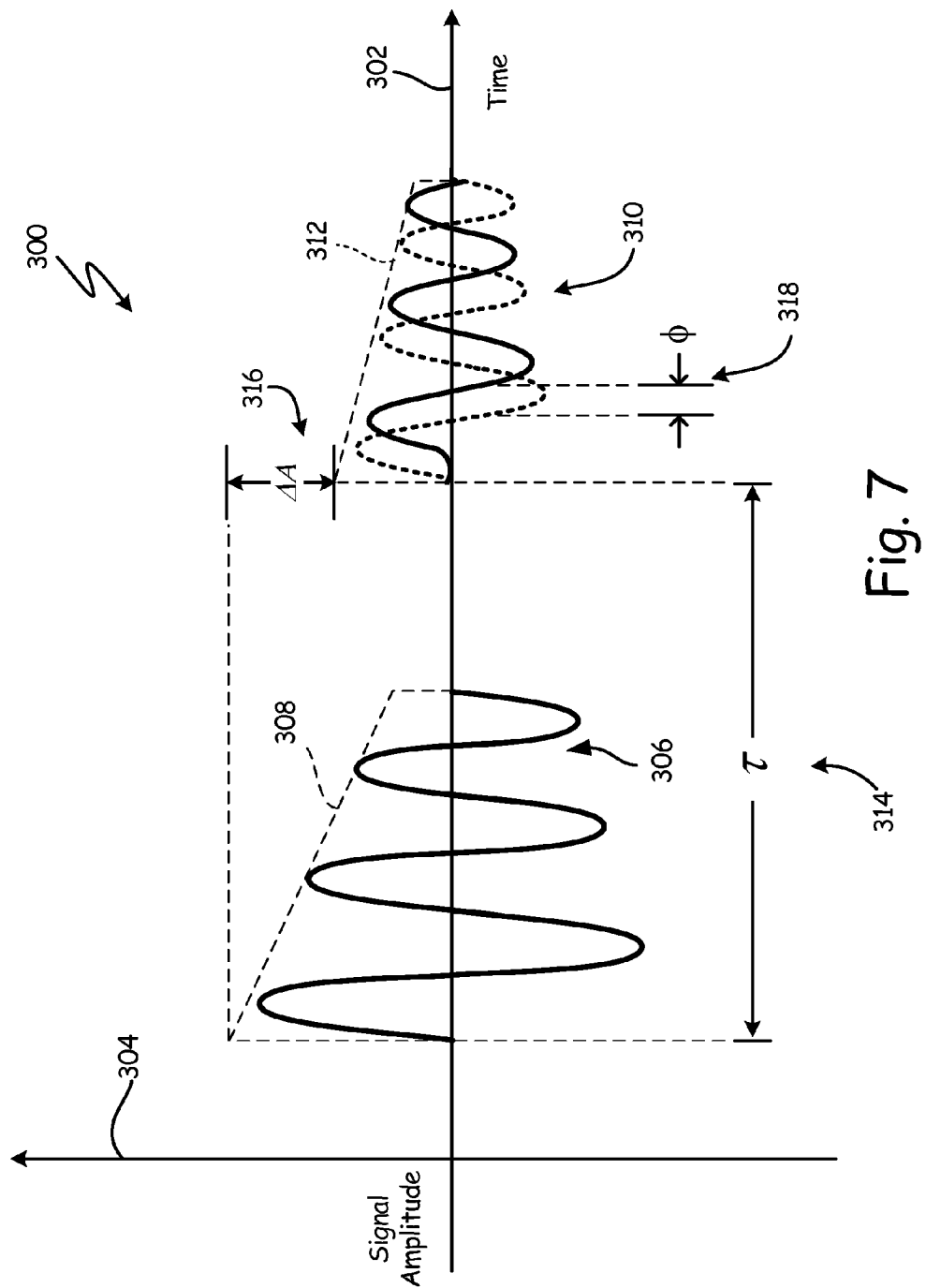
FIG. 7 is a graph of an exemplary signal transmitted to a linear thermal sensor and an exemplary reflection signal received from the linear thermal sensor.

FIG. 7 is a graph of an exemplary signal transmitted to a linear thermal sensor and an exemplary reflection signal received from the linear thermal sensor. Graph 300 includes horizontal axis 302, which indicates time. Graph 300 includes vertical axis 304, which indicates signal amplitudes. Signal portions 306, 310 correspond to the signal delivered to analyzer 218 by sense amplifier 216 in FIG. 6. Signal 306 represents the generated signal portion, and signal 310 represents the reflected signal portion. Note that both generated signal portion 306 and reflected signal portion 310 are damped sinusoidal impulse signals. Each of signals 306, 310 have amplitude envelopes 308, 312, respectively, that are damped. Each of signals 306, 310 have three periods of a sinusoid.

Signals 306 and 310 differ, however, in at least three ways. First, amplitude difference 316 shows that reflected signal portion 310 is smaller than generated signal portion 306. Second, time delay 314 shows that reflected signal portion 310 is delayed with respect to generated signal portion 306. Third, phase difference 318 shows that reflected signal 310 is phase delayed, with respect to amplitude envelope 312 as compared with a phase of generated signal 306 with respect to amplitude envelope 308. Phase difference 318 and amplitude difference 316 can be used to calculate the nature of the electrical discontinuity the caused reflection signal portion 310. Time delay 314 can be used to determine a location of the electrical discontinuity that caused reflection signal portion 310.

In the depicted embodiment, time delay 314 is longer than a time that amplitude envelopes, 308, 312 are non-zero. In such an embodiment, reflected signal portion 310 is separated from or non-overlapping of generated signal portion 306. In some embodiments, time delay 314 can be smaller than the time that amplitude envelopes 308, 312 are non-zero. In such embodiments, reflected signal portion 310 can overlap generated signal portion 306. Analyzer 218 of FIG. 6 can then determine time delay 314, amplitude difference 316, and phase difference 318 from the overlapping signal portions 306, 310. Various means for determined such metrics can be used. For example, reflected signal portion 310 can be mixed with generated signal portion 306. The mixed signal can be filtered. Metrics can then be extracted from the filtered mixed signal, for example. Another exemplary embodiment may perform a Fast Fourier Transform (FFT) on the overlapping signals. The FFT can then be used to extract the metrics, using phase angles, amplitudes, etc.

Figure 8:
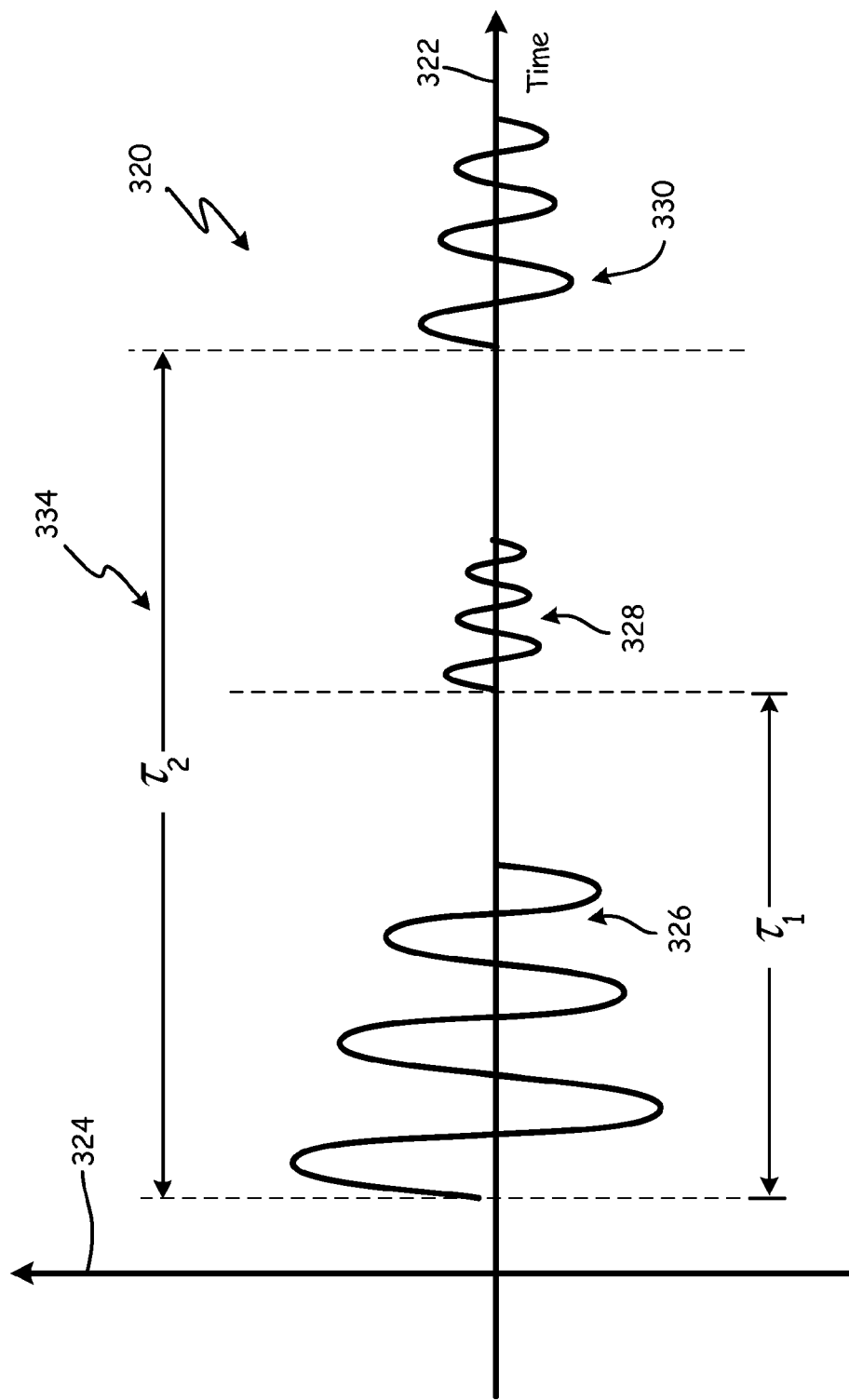
FIG. 8 is a graph of an exemplary signal transmitted to a linear thermal sensor and two reflection signals received from the linear thermal sensor.

FIG. 8 is a graph of an exemplary signal transmitted to a linear thermal sensor and two reflection signals received from the linear thermal sensor. In FIG. 8, graph 320 includes horizontal axis 322 and vertical axis 324. Horizontal axis 322 indicates time and vertical axis 324 indicates signal amplitudes. Signal portions 326, 328, 330 again correspond to the signal delivered to analyzer 218 by sense amplifier 216 in FIG. 6. In the FIG. 8 graph, signal portion 326 represents the generated signal portion, and signals 328, 330 represent two different signal portions reflected from two different electrical discontinuities, respectively, in linear thermal sensor 20. First reflection portion 328 has time delay 332 with respect to generated signal portion 326. Second reflection portion 330 has time delay 334 with respect to generated signal portion 326.

A frequency of generated signal portion 326 may have been selected so that generated signal portion 326 traversed a first electrical discontinuity associated with reflected signal portion 328. Such a selection of frequency can facilitate the ability of a testing system to "see beyond" a first discontinuity and facilitate the ability to determine the electrical characteristic and location of a subsequent discontinuity. Such a subsequent discontinuity may be associated with reflected signal portion 330, for example. When generated signal portion 326 has a frequency that traverses an electrical discontinuity, the traversed electrical discontinuity may only reflect a small fraction of generated signal portion 326 incident thereto. Thus, reflected signal portion 328 is depicted as having a relatively-small amplitude with respect to generated signal portion 326.

Because only a small fraction of generated signal portion 326 is reflected by a first electrical discontinuity, a large fraction of the incident signal thereto may continue along linear thermal sensor 20. This fraction that continues along linear thermal sensor 20 may then encounter a second electrical discontinuity, which in turn reflects a fraction of the signal incident thereto. Because a large fraction of generated signal portion 326 is incident to the second electrical discontinuity, reflected signal portion 330 associated with the second electrical discontinuity may have an amplitude that is larger than if only a small fraction of generated signal portion 326 had been incident thereto. A large-amplitude reflected signal portion 330 may better facilitate determining the electrical nature and location of the second electrical discontinuity than would be facilitated by a small amplitude reflected signal portion.

Figure 9:
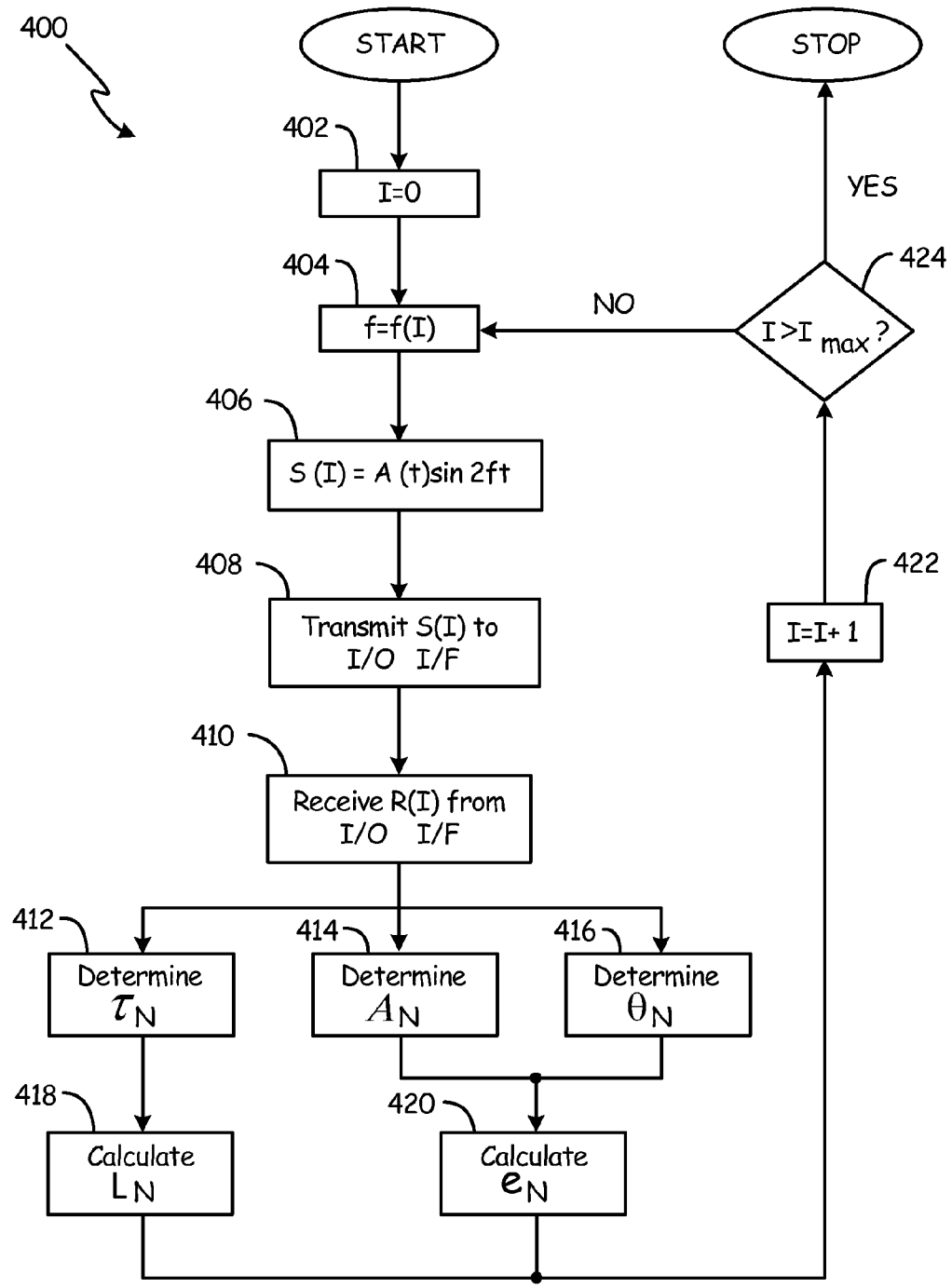
FIG. 9 is a flow chart of an exemplary method of testing linear thermal sensors.

FIG. 9 is a flow chart of an exemplary method of testing linear thermal sensors. In FIG. 9, method 400 for testing a linear thermal sensor is shown from the perspective view of testing system 202 depicted in FIG. 6. Method 400 begins by initializing a counter, I, at step 402. Then at step 404, a frequency associated with counter, I, is selected. At step 406, signal generator 210 generates damped sinusoidal impulse signal, S, having frequency, f, and amplitude envelope, A. At step 408, signal generator 210 transmits the generated signal to an input/output interface for electrical communication with linear thermal sensor 20. At step 410, testing system receives reflected signal, R, corresponding to generated signal, S.

At step 412, signal analyzer 218 determines one or more delay times, $\tau_N$, of reflected portions corresponding to one or more electrical discontinuities, respectively. At step 414, signal analyzer 218 determines one or more amplitudes, $A_N$, of reflected portions corresponding to the one or more electrical discontinuities, respectively. At step 416, signal analyzer 218 determines one or more phase differences, $\varphi_N$, between reflected portions corresponding to the one or more electrical discontinuities, respectively, and the generated damped sinusoidal impulse signal. At step 418, signal analyzer 218 calculates locations, $L_N$, corresponding to the one or more electrical discontinuities, based on the determined values of $A_N$ and $\varphi_N$. At step 420, signal analyzer 218 calculates electrical parameters, $e_N$, corresponding to the one or more electrical discontinuities, based on the determined value of $\tau_N$. Index, I, is incremented at step 422. At step 424, Index I is compared with maximum index, $I_{MAX}$. If, at step 424, index, I, is not greater than maximum index, $I_{MAX}$, then method 400 returns to step 404 and selects a new frequency, f, associated with the new index, I. If, however, at step 424, index, I, is greater than maximum index, $I_{MAX}$, then method 400 ends.

Figure 10:
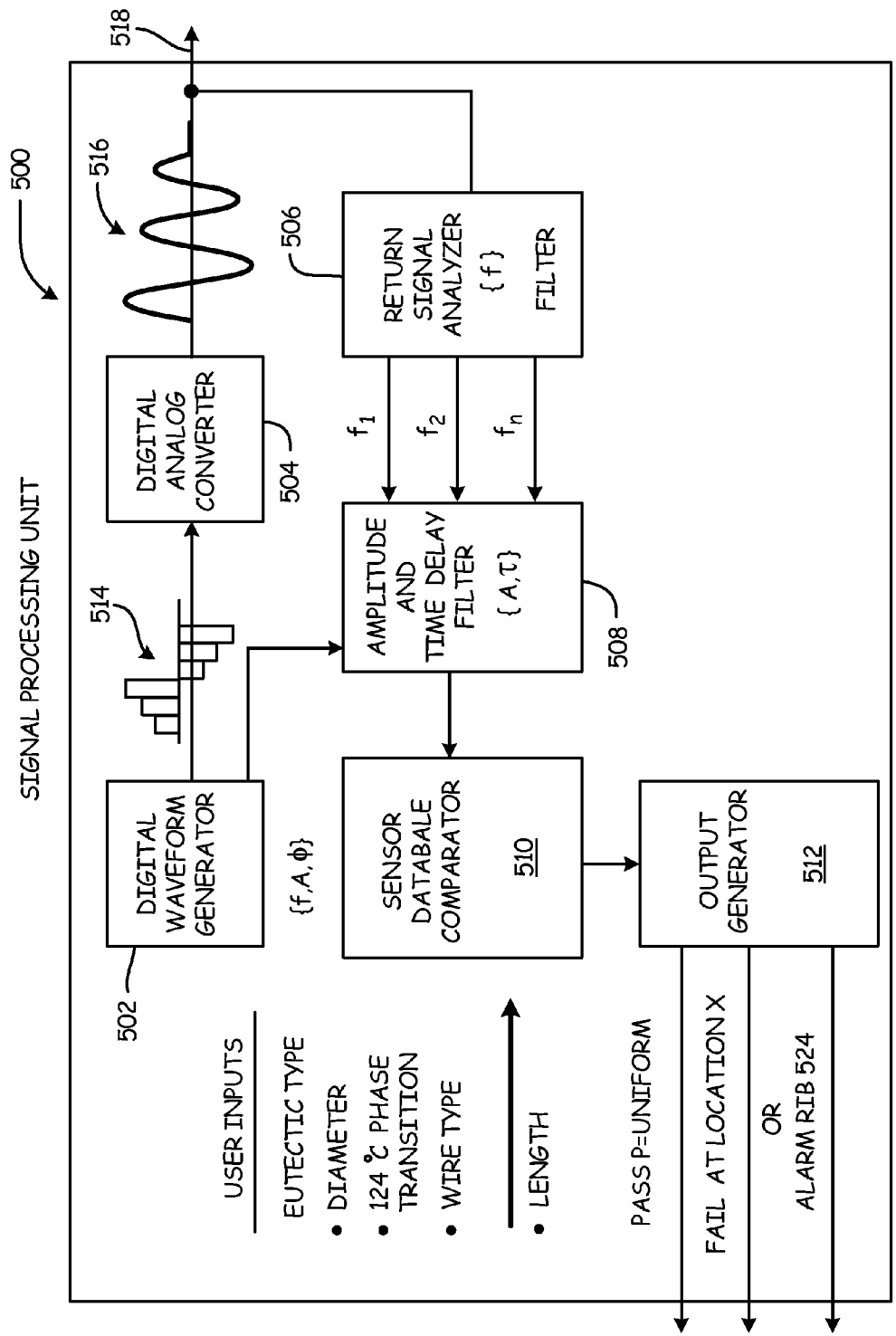
FIG. 10 is a block diagram of an exemplary signal processing unit for a multi-function over-temperature detection system.

FIG. 10 is a block diagram of an exemplary signal processing unit for a multi-function over-temperature detection system. In FIG. 10, exemplary signal processing unit 500 includes digital waveform generator 502, digital to Analog Converter 504, return signal analyzer filter 506, amplitude and time-delay filter 508, sensor database comparator 510 and output generator 512. Digital waveform generator 502 creates digital waveform 514 that corresponds to damped sinusoidal impulse signal 516 having a predetermined frequency, amplitude envelope, and phase. Digital to analog converter 504 receives created digital waveform 514 and converts it to analog form as damped sinusoidal impulse signal 516. Damped sinusoidal impulse signal 516 is then delivered to output node 518 for delivery to a linear thermal sensor.

Output node 518 is also coupled to return signal analyzer filter 506, which filters noise from signal sensed on output node 518. Output node 518 carries both damped sinusoidal impulse signal 516 and any signals reflected from a connected linear thermal sensor and/or array. Return signal analyzer filter 506 may determine frequencies of such reflected signals and may deliver the filtered reflected signals to amplitude and time delay filter 508. Amplitude and time delay filter 508 may then determine an amplitude envelope and time delay corresponding to each of filtered reflected signals received from return signal analyzer filter 506.

Sensor database comparator 510 receives reflected signal metrics determined by amplitude and time-delay filter and/or return signal analyzer filter. Sensor database comparator 510 then compares the received reflected signal metrics with a stored database of metrics. These stored metrics may include metrics that represent good and/or bad sensors, for example. These metrics may include metrics that correspond with expected and/or unexpected reflection times, and or reflection amplitudes, for example. Sensor database comparator 510 then sends a signal corresponding to the comparison results to output generator 512. Output generator 512 may have two modes of operation. Output generator 512 may have a test mode in which pass/fail results are provided to one or more output nodes. For example output generator 512 may provide a pass/fail signal to an output node. If the pass/fail signal is indicative of a failing linear thermal sensor, output generator may provide a signal corresponding to a failing location of the linear thermal sensor to an output node. In generator 512 may have an operation mode, in an alarm signal is generated if the linear thermal sensor indicates an over-temperature condition, for example. Output generator 512 may provide this alarm signal to an output node if the reflected signal is indicative of such an over-temperature condition. A location of such an over-temperature condition may also be communicated via a location signal to an output node.

Figure 11:
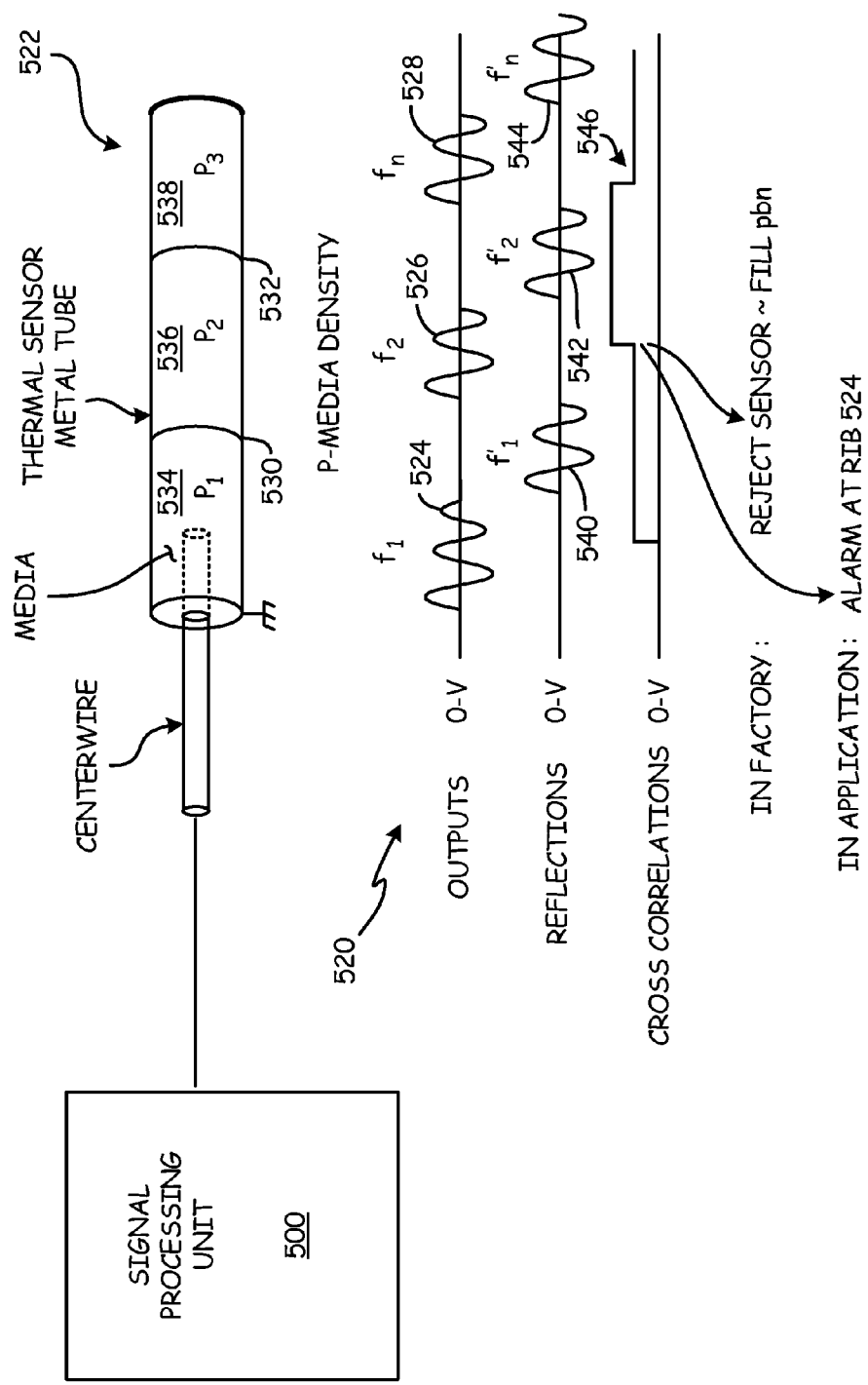
FIG. 11 is a schematic of an exemplary signal produced by an exemplary multi-function over-temperature detection system.

FIG. 11 is a schematic of an exemplary signal produced by an exemplary multi-function over-temperature detection system. In FIG. 11, signal processing unit 500 generates series 520 of damped sinusoidal impulse signals 524, 526, 528 to linear thermal sensor 522. Linear thermal sensor 522 reflects each of damped sinusoidal impulse signals 524, 526, 528 at each of discontinuities 530, 532 between adjacent regions of different media densities 534, 536, 538. Each of reflected signals 540, 542, 544 is then analyzed by signal processing unit 500. Signal processing unit 500, may, for example, perform cross-correlation FFT operations using reflected signals 540, 542, 544 and damped sinusoidal impulse signals 524, 526, 528. Each cross-correlation FFT operation may provide metrics of time-delay, amplitude, and/or phase information. Signal processing unit 500 may, for example, calculate media density information 546 from reflected signals 540, 542, 544, for example.

Signal processing unit 500 may have a factory mode and/or an application mode, for example. In factory mode, signal processing unit 500 may determine pass/fail metrics of tested linear thermal sensors. In application mode, signal processing unit 500 may provide continuous monitoring of a linear thermal sensor array for over-temperature hazards.

Various embodiments may be used in various manners. For example, in some embodiments, linear-thermal-sensor testing systems may be used during manufacture of linear thermal sensors. Such testing systems may be used to determine whether each particular sensor meets a predetermined specified standard, for example. Such testing systems may be used to determine a quality metric of a particular composition of a eutectic salt bath, for example. Various embodiments may be used in an operation manner. For example, in some embodiments, linear-thermal-sensor testing systems may be operationally coupled to a linear thermal sensor during standard flight operation. Such testing systems may report status of plenums, manifold, or ductwork in real time to a pilot, for example. Should d a testing system indicate an over-temperature condition, the testing system then might provide specific location where such an over-temperature condition is experienced. This location information can facilitate a pilot's response to the over-temperature condition.

Apparatus and associated methods relate to a linear-thermal-sensor testing system that includes a signal generator that is configured to generate a series of damped sinusoidal impulse signals each of a different frequency, and transmit the damped sinusoidal impulse signals to a first end of a linear thermal sensor. The linear thermal sensor is configured to generate a reflection signal corresponding to each of the series of damped sinusoidal impulse signals at one or more electrical discontinuities in the linear thermal sensor. The linear-thermal-sensor testing system includes a reflection analyzer that is configured to receive a reflection signal from the first end of the linear thermal sensor. The reflection signal has indicia of electrical properties and locations within the linear thermal sensor for each of the one or more electrical discontinuities. The reflection analyzer is further configured to calculate the electrical properties and the locations within the linear thermal sensor based on the indicia of the received reflection signal.

The linear-thermal-sensing system of the preceding paragraph can optionally include, additionally and/or alternatively, a series connected array of linear thermal sensors. A further embodiment of any of the foregoing linear-thermal-sensing system, wherein the one or more electrical discontinuities may include at least an insertion discontinuity proximate the first end of the linear thermal sensor and/or a terminal discontinuity at a second end of the linear thermal sensor. A further embodiment of any of the foregoing linear-thermal-sensing system, wherein each of the damped sinusoidal impulse signals may comprise between 2 and 10 cycles of a sinusoid each, all having substantially the same period. A further embodiment of any of the foregoing linear-thermal-sensing system, wherein each of the damped sinusoidal impulse signals may comprise between 3 and 5 cycles of a sinusoid each, all having substantially the same period.

A further embodiment of any of the foregoing linear-thermal-sensing system, wherein a first cycle may have a largest amplitude and each of subsequent cycles may have an amplitude that is less than or equal to an amplitude of all cycles preceding it. A further embodiment of any of the foregoing linear-thermal-sensing system, wherein the reflection analyzer may be further configured to compare the received reflection signal with a signature signal that is representative of a linear thermal sensor that meets a predetermined specification standard. A further embodiment of any of the foregoing linear-thermal-sensing system, wherein the linear thermal sensor may comprise a coaxial eutectic sensor. A further embodiment of any of the foregoing linear-thermal-sensing system, wherein the linear thermal sensor comprises a thermistor sensor.

A further embodiment of any of the foregoing linear-thermal-sensing system, wherein the frequency of each of the damped sinusoidal impulse signals of the generated series is less than 100 kHz. A further embodiment of any of the foregoing linear-thermal-sensing system, wherein the frequency of each of the damped sinusoidal impulse signals of the generated series is less than 20 kHz. A further embodiment of any of the foregoing linear-thermal-sensing system, wherein the reflection analyzer is further configured to mix the received reflection signal with the generated damped sinusoidal impulse signal. A further embodiment of any of the foregoing linear-thermal-sensing system, wherein the frequency of at least one of the damped sinusoidal impulse signals of the generated series is configured to traverse a first of the one or more electrical discontinuities.

In some embodiments, a method of testing a linear thermal sensor includes the step of generating a series of damped sinusoidal impulse signals each of a different frequency. The method includes the step of transmitting the generated series of damped sinusoidal impulse signals to a first end of the linear thermal sensor. The method includes the step of receiving, at the first end of the linear thermal sensor, a series of reflection signals each corresponding to a one of the series of damped sinusoidal impulse signals. Each of the reflection signals is reflected by one or more electrical discontinuities in the linear thermal sensor. The method includes the step of determining an amplitude of the received reflected signal. The method includes the step of determining a time-delay of the received reflected signal. The method includes the step of calculating an electrical property of an electrical discontinuity in the linear thermal sensor based on the determined amplitude and phase shift of the received reflected signal.

The testing method of the preceding paragraph can optionally include, additionally and/or alternatively, any one or more of the following features, configurations and/or additional components: i) determining a phase shift of the received reflected signal; ii) calculating a location of the electrical discontinuity in the linear thermal sensor based on the determined time delay of the received reflected signal; iii) comparing the received reflection signal with a signature signal that is representative of a linear thermal sensor that meets a predetermined specification standard; and iv) mixing the received reflection signal with the generated damped sinusoidal impulse signal.

A further embodiment of any of the foregoing fan drive gear system, wherein generating a series of damped sinusoidal impulse signals may include generating between 2 and 10 cycles of a sinusoid each. A further embodiment of any of the foregoing fan drive gear system, wherein generating a series of damped sinusoidal impulse signals may include generating between 3 and 5 cycles of a sinusoid each. A further embodiment of any of the foregoing fan drive gear system, wherein generating a series of damped sinusoidal impulse signals may include generating a decaying amplitude envelope, wherein a first cycle may have the largest amplitude and each subsequent cycle may have an amplitude envelope that is less than or equal to an amplitude envelope of all cycles preceding it. A further embodiment of any of the foregoing fan drive gear system, wherein generating a series of damped sinusoidal impulse signals may include generating at least one damped sinusoidal impulse signal configured to traverse a first of the plurality of electrical discontinuities.

While the invention has been described with reference to an exemplary embodiment(s), it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment(s) disclosed, but that the invention will include all embodiments falling within the scope of the appended claims.

The invention claimed is:

1. A linear-thermal-sensor testing system comprising:
   a signal generator that is configured to generate a series of damped sinusoidal impulse signals, each of a different frequency, and transmit the damped sinusoidal impulse signals to a first end of a linear thermal sensor, wherein the linear thermal sensor is configured to generate a reflection signal corresponding to each of the series of damped sinusoidal impulse signals at one or more electrical discontinuities in the linear thermal sensor;
   a reflection analyzer that is configured to receive a reflection signal from the first end of the linear thermal sensor, the reflection signal having indicia of locations and indicia of electrical properties of the one or more electrical discontinuities in the linear thermal sensor, wherein the reflection analyzer is further configured to calculate the locations and the electrical properties of the one or more discontinuities in the linear thermal sensor based on the indicia of the received reflection signal.

2. The linear-thermal-sensor testing system of claim 1, wherein the one or more electrical discontinuities includes at least an insertion discontinuity proximate the first end of the linear thermal sensor and a terminal discontinuity at a second end of the linear thermal sensor.

3. The linear-thermal-sensor testing system of claim 1, wherein each of the damped sinusoidal impulse signals comprises between 2 and 10 cycles of a sinusoid each, all having substantially the same period.

4. The linear-thermal-sensor testing system of claim 1, wherein each of the damped sinusoidal impulse signals comprises between 3 and 5 cycles of a sinusoid each, all having substantially the same period.

5. The linear-thermal-sensor testing system of claim 1, wherein each the damped sinusoidal impulse signals has a decaying amplitude envelope, wherein a first cycle has a largest amplitude and each of subsequent cycles has an amplitude that is less than or equal to an amplitude of all cycles preceding it.

6. The linear-thermal sensor testing system of claim 1, wherein the reflection analyzer is further configured to compare the received reflection signal with a signature signal that is representative of a linear thermal sensor that meets a predetermined specification standard.

7. The linear-thermal sensor testing system of claim 1, wherein the linear thermal sensor comprises a coaxial eutectic sensor.

8. The linear-thermal sensor testing system of claim 1, wherein the linear thermal sensor comprises a thermistor sensor.

9. The linear-thermal sensor testing system of claim 1, further comprising a series connected array of linear thermal sensors.

10. The linear-thermal-sensor testing system of claim 1, wherein the frequency of each of the damped sinusoidal impulse signals of the generated series is less than 100 kHz.

11. The linear-thermal-sensor testing system of claim 1, wherein the frequency of each of the damped sinusoidal impulse signals of the generated series is less than 20 kHz.

12. The linear-thermal sensor testing system of claim 1, wherein the reflection analyzer is further configured to mix the received reflection signal with the generated damped sinusoidal impulse signal.

13. The linear-thermal sensor testing system of claim 1, wherein the frequency of at least one of the damped sinusoidal impulse signals of the generated series is configured to traverse a first of the one or more electrical discontinuities.

14. A method of testing a linear thermal sensor, the method comprising the steps of:
   generating a series of damped sinusoidal impulse signals, each of a different frequency;
   transmitting the generated series of damped sinusoidal impulse signals to a first end of the linear thermal sensor;
   receiving, at the first end of the linear thermal sensor, a series of reflection signals, each corresponding to one of the damped sinusoidal impulse signals of the generated series, each of the reflection signals being reflected by one or more electrical discontinuities in the linear thermal sensor;
   determining an amplitude of the received reflected signal;

determining a time-delay of the received reflected signal; and calculating an electrical property of an electrical discontinuity in the linear thermal sensor based on the determined amplitude and phase shift of the received reflected signal.

15. The method of claim 14, further comprising determining a phase shift of the received reflected signal.

16. The method of claim 14, further comprising calculating a location of the electrical discontinuity in the linear thermal sensor based on the determined time delay of the received reflected signal.

17. The method of claim 14, wherein generating a series of damped sinusoidal impulse signals comprises generating between 2 and 10 cycles of a sinusoid each.

18. The method of claim 14, wherein generating a series of damped sinusoidal impulse signals comprises generating between 3 and 5 cycles of a sinusoid each.

19. The method of claim 14, wherein generating a series of damped sinusoidal impulse signals comprises generating a decaying amplitude envelope, wherein a first cycle has the largest amplitude and each subsequent cycle has an amplitude envelope that is less than or equal to an amplitude envelope of all cycles preceding it.

20. The method of claim 14, further comprising comparing the received reflection signal with a signature signal that is representative of a linear thermal sensor that meets a predetermined specification standard.

21. The method of claim 14, further comprising mixing the received reflection signal with the generated damped sinusoidal impulse signal.

22. The method of claim 14, wherein generating a series of damped sinusoidal impulse signals comprises generating at least one damped sinusoidal impulse signal configured to traverse a first of the plurality of electrical discontinuities.

* * * * *